(12) United States Patent
Nagel et al.

(10) Patent No.: US 10,156,533 B2
(45) Date of Patent: Dec. 18, 2018

(54) METHOD FOR MANUFACTURING AN INDUCTIVE CONDUCTIVITY SENSOR AND INDUCTIVE CONDUCTIVITY SENSOR

(71) Applicant: Endress + Hauser Conducta Gesellschaft für Mess—und Regeltechnik mbH + Co. KG, Gerlingen (DE)

(72) Inventors: Thomas Nagel, Wilsdruff (DE); Andre Pfeifer, Schkopau (DE)

(73) Assignee: Endress+Hauser Conducta GmbH+Co. KG, Gerlingen (DE)

( * ) Notice: Subject to any disclaimer, the term of this patent is extended or adjusted under 35 U.S.C. 154(b) by 670 days.

(21) Appl. No.: 14/817,535

(22) Filed: Aug. 4, 2015

(65) Prior Publication Data

US 2016/0061759 A1    Mar. 3, 2016

(30) Foreign Application Priority Data

Aug. 7, 2014  (DE) ..................... 10 2014 111 265

(51) Int. Cl.
| | |
|---|---|
| *B32B 37/00* | (2006.01) |
| *G01N 27/02* | (2006.01) |
| *B23K 20/10* | (2006.01) |
| *H01F 27/02* | (2006.01) |
| *H01F 38/20* | (2006.01) |
| *B23K 101/42* | (2006.01) |

(52) U.S. Cl.
CPC ........... *G01N 27/025* (2013.01); *B23K 20/10* (2013.01); *H01F 27/02* (2013.01); *H01F 38/20* (2013.01); *B23K 2201/42* (2013.01)

(58) Field of Classification Search
CPC ...... B29C 65/08; B23K 20/10; G01N 27/025; H01F 27/02; H01F 38/20
USPC ........................................................ 156/73.1
See application file for complete search history.

(56) References Cited

U.S. PATENT DOCUMENTS

| | | | |
|---|---|---|---|
| 4,259,419 A | 3/1981 | Uba et al. | |
| 4,993,007 A * | 2/1991 | Meister ................. | B29C 65/645 156/73.1 |

(Continued)

FOREIGN PATENT DOCUMENTS

| | | |
|---|---|---|
| CN | 2593202 Y | 12/2003 |
| CN | 103869174 A | 6/2014 |
| DE | 19508221 C1 | 9/1996 |

*Primary Examiner* — James D Sells
(74) *Attorney, Agent, or Firm* — Christopher R. Powers; PatServe (57) ABSTRACT

A method for manufacturing an inductive conductivity sensor, wherein on both sides of a circuit board coils are placed surrounding an opening of the circuit board, and the circuit board with the coils is inserted into a housing. A sleeve is inserted through a first opening of the housing through the opening of the circuit board into the housing. The sleeve includes a first end section and a second end section and the sleeve is inserted with the first end section first into the housing, and wherein the sleeve is welded with the housing by means of a sonotrode by ultrasonic welding. Both the first end section as well as also the second end section of the sleeve are welded with the housing, wherein the sonotrode is applied exclusively on the sleeve on the side of the second end section. The invention relates further to an inductive conductivity sensor.

9 Claims, 4 Drawing Sheets

(56) References Cited

U.S. PATENT DOCUMENTS

| | | |
|---|---|---|
| 7,037,393 B2 * | 5/2006 | Drummond .......... B01D 53/268 156/69 |
| 2008/0028593 A1 | 2/2008 | Friedrichs et al. |
| 2012/0098550 A1 | 4/2012 | Fanselow et al. |

* cited by examiner

METHOD FOR MANUFACTURING AN INDUCTIVE CONDUCTIVITY SENSOR AND INDUCTIVE CONDUCTIVITY SENSOR

TECHNICAL FIELD

The invention relates to a method for manufacturing an inductive conductivity sensor and to an inductive conductivity sensor produced by such a method.

BACKGROUND DISCUSSION

Inductive conductivity sensors serve in a large number of applications in laboratory and process measurements technology for registering the conductivity of a liquid medium. They are used preferably where large measuring ranges and high chemical or thermal loadings occur. This is the case, for example, in a large number of industrial chemical processes and also in hot steam sterilization methods, which are frequently applied in foods technology due to the high hygiene requirements.

As a result of the mentioned requirements, frequently high performance plastics are used. Polyetheretherketone (abbreviated PEEK) is an example of a high temperature resistant, thermoplastic, synthetic material and is a member of the group, polyaryletherketones. Polyetheretherketone (PEEK) is a partially crystalline thermoplastic with high tensile- and bending strength, high impact toughness, high fatigue strength, high chemical resistance and is only difficultly burnable.

An inductive conductivity sensor includes a transmitting coil and a receiving coil, which, as a rule, are embodied as ring coils, also referred to as toroidal coils. Such a conductivity sensor functions as a type of double transformer, wherein the transmitting and receiving coils are inserted so far into the medium that a closed electrical current path can form extending through the medium and passing through the transmitting and receiving coils. When the transmitting coil is excited with an alternating voltage signal as an input signal, it produces a magnetic field, which induces in the closed path through the medium passing through the coils an electrical current, whose strength depends on the electrical conductivity of the medium. Since this alternating electrical current in the medium brings about, in turn, a variable magnetic field surrounding it, an alternating electrical current is induced in the receiving coil as an output signal. This alternating electrical current, respectively a corresponding alternating voltage, delivered from the receiving coil as an output signal is a measure for the electrical conductivity of the medium.

For feeding the transmitting coil with an alternating voltage, an inductive conductivity sensor includes a driver circuit connected with the transmitting coil. For registering the output signal of the receiving coil, the conductivity sensor includes, moreover, electrically connected with the receiving coil, a receiving circuit, which is embodied to output the registered measurement signal, in given cases, conditioned by the receiving circuit, to a sensor electronics, which serves to process the measurement signal further and, in given cases, to digitize it. Frequently, conductivity sensors are embodied as measuring probes at least sectionally immersible in the medium. Such measuring probes include a housing, in which the transmitting and receiving coils, in given cases, the driver circuit and the receiving circuit as well as other circuit parts assembled with the transmitting and receiving circuit into a sensor circuit, are accommodated. The measuring probe is connected in such an embodiment with a removed, superordinated unit, for example, a display unit, a measurement transmitter, or a computer. The superordinated unit can be embodied both for energy supply of the measuring probe as well as also for data communication with the measuring probe. The sensor circuit optionally contained in the measuring probe can be embodied to forward the further processed, in given cases, digitized, measurement signal to the superordinated unit. The corresponding measured value can be displayed via the superordinated unit by means of a display system or output via a data interface.

The coils of the inductive conductivity sensors can be provided with a housing in various ways. In one known method, a coil component is formed, in the case of which the coils are, first of all, in a complex method, introduced into a separate coil housing and then injection molded around, in this coil housing, with plastic. The so produced assembly is then inserted into a sensor housing. The creating of the separate coil housing is necessary, in order to protect the coils in the injection molding from the high injection pressures and very high temperatures during the injection procedure. Since the coils are very sensitive to pressure and temperature, there is present in this processing besides a high preparation- and assembly effort for the coil component a high rejection risk.

In the case of a known sensor, two coils are arranged, in each case, on a side of a circuit board and then the prefabricated circuit board inserted into the sensor housing. The circuit board includes, in such case, an opening, in order to position the coils in the form of toroidal coils. After the insertion of the circuit board into the sensor housing, the housing is sealed by a sleeve, which is inserted through a wall of the housing into the housing and guided through the opening of the circuit board. The two ends of the sleeve are, in such case, adhered to the housing at the interfaces with such. The inner space of the sensor housing is, in this connection, filled with a potting compound. Besides the preparation effort for the adhesive locations, which must be cleaned before the adhesion process, also a rework of the adhesive at the transition locations is necessary. The adhesive gap, which forms between sleeve and housing, has a different coefficient of thermal expansion than the housing, wherein in the case of temperature changes during use of the inductive sensor the adhesive gap can be damaged. Moreover, the adhesive has a lesser chemical durability than the plastic. For manufacturing the two separate adhesive locations, a complex handling is necessary, which lengthens the time required for the procedure.

Known from German Patent DE 10 2010 042 832 is a process utilizing ultrasonic welding.

The dissertation of Joachim Nehr with the title "Neuro-Fuzzy-Modellierung zur umfassenden Prozessüberwachung am Beispiel des Ultraschallschweißens von Kunststoffteilen (neuro-fuzzy modeling for comprehensive process monitoring in the example of ultrasonic welding of plastic parts)", Universitat Stuttgart (University of Stuttgart), year 2011, describes the ultrasonic welding process in the following way: An oscillatable system, composed of converter, booster and sonotrode, is caused to oscillate with longitudinal oscillations in the ultrasonic region by excitation by means of piezo elements in the converter. Typical oscillation frequencies are, in such case, 20, 30, 35 or 40 kHz, depending on machine manufacturer and size of the workpieces to be welded. The initial oscillation amplitude in the range from about 6 to 13 µm—depending on oscillation frequency—is amplified by the booster (also called the amplitude transformer) and the sonotrode application- and material specifically by a factor in the range, 1-5. By mechanical coupling of the sonotrode, the oscillation is introduced into the workpiece. The oscillatory energy is absorbed by inner friction and boundary friction, whereupon the occurring heat leads to a local melting in the joint zone and thereby to connection of the two joint partners.

The process flow in the case of ultrasonic welding is divided into three phases: 1) The start, wherein the sonotrode acts on the components to be connected and the mechanical coupling occurs with a selectable force; 2) The actual welding phase, during which the oscillation produced by the converter is introduced into the component at a given force level and leads to melting and connecting of the components; and 3) The holding phase for cooling the melt arising in the welding until the solid weld seam forms.

Depending on separation between weld zone and sonotrode where the oscillation is being introduced, a distinction is drawn between near field and far field welding, wherein a separation of about 6 mm marks the border between the two types of welding. Far field welds can be performed best with stiff thermoplastics, since an upturning of the parts related to the welding force should be kept as small as possible or completely prevented. Due to the shear modulus and mechanical loss factor, most often, only amorphous synthetic materials are welded in the far field. Partially crystalline plastic materials, which, most often, have a marked damping rise already well below the melting temperature, should only be welded in the near field.

SUMMARY OF THE INVENTION

An object of the invention is to provide a method for manufacturing an inductive conductivity sensor, in the case of which the handling during the connecting process of the sleeve with the housing is simplified and, while avoiding a high preparation effort, a stable connection between sleeve and housing is achieved.

The object is achieved by a method wherein on both sides of a circuit board coils are placed surrounding an opening of the circuit board and the circuit board with the coils is inserted into a housing, wherein a sleeve is inserted through a first entrance of the housing through the opening of the circuit board into the housing, wherein the sleeve includes a first end section and a second end section and the sleeve is inserted with the first end section first into the housing, and wherein the sleeve is welded with the housing by means of a sonotrode by ultrasonic welding. The method is characterized in that both the first end section as well as also the second end section of the sleeve are welded with the housing, wherein the sonotrode is applied exclusively on the sleeve on the side of the second end section.

The manufacturing effort is, thus, lessened compared to the state of the art and the entire manufacturing process is simplified. Compared to an adhesive connection, higher strengths are achieved while quality remains the same. Moreover, the new method is environmentally friendly, since no solvents are used.

Usually, ultrasonic welding is performed either in the far field or in the near field. Here, however, preferably, simultaneously, the first end section of the sleeve is welded with the housing by means of far field welding and the second end section by means of near field welding.

In an advantageous embodiment, a shear joint is used for forming a seam geometry of a first weld seam, wherein the first end section of the sleeve includes a first energy concentrator, in the following named the first concentrator, and the first concentrator serves for forming the first weld seam with a first planar area of the housing in the region of the first end section. In an alternative advantageous embodiment, the concentrator is located on the housing and interacts with a first planar area on the sleeve.

A concentrator is in general a structural feature, which brings something together, focuses, respectively compacts. In the sense of this invention, "concentrator" means concentrated melting region, thus the region where, due to a certain structure and geometry, the material begins to melt due to the ultrasonic welding.

In a preferred further development, a shear joint is used for forming a seam geometry of a second weld seam, wherein the housing includes a wedge shaped profile, and the wedge shaped profile serves for forming the second weld seam with a second planar area of the sleeve in the region of the second end section. In an alternative preferred further development, the sleeve includes a wedge shaped profile and interacts with a second planar area of the housing.

In an advantageous embodiment, a shear joint is used for forming a seam geometry of a third weld seam, wherein the housing includes a second energy concentrator, named the second concentrator in the following, and the second concentrator, for forming the third weld seam, interacts with an inclined area of the sleeve in the region of the second end section. In an alternative advantageous embodiment, the sleeve includes a second concentrator and interacts with an inclined area of the housing.

Preferably, at least one of the above described concentrators has a V-shaped profile with an acute angle between 90° and 60°, a triangular profile, a rectangular profile or a half round profile. In this way, the energy can be optimally in-coupled. In other words, the concentrator is formed by a V-shaped profile having an acute angle between 90° and 60°, a triangular profile, a rectangular profile or a half round profile. In the sense of this invention, the "concentrator" includes a first section having a minimum bearing surface on the workpiece to be welded and a second section. During the welding, the concentrator melts up to the second section.

In the sense of this invention, indeed, a distinction is made between a "concentrator" and a "wedge shaped profile". Nevertheless, the "wedge shaped profile" can also be embodied as a V-shaped profile having an acute angle between 90° and 60°, a triangular profile, a rectangular profile or a half round profile. In their embodiment, thus material, geometry and structure, the two can, thus, be equal and achieve, thus, also the same result.

Following the welding, there is thus obtained a single part, which is composed of two different portions. However, a single homogeneous part is not obtained. Thus, the weld seams are visible after the welding.

In an advantageous further development, welding proceeds in the time sequence first weld seam, second weld seam, third weld seam, wherein the first weld seam, second weld seam and third weld seam are for a certain time simultaneously molten.

For preventing long heat up phases, welding occurs advantageously at room temperature.

In a preferred further development, the sleeve welded with the housing is further worked, especially rounded, in the first end region and/or in the second end region. Thus, the conductivity sensor manufactured with the method then meets hygienic requirements. Possibly present cavities, corners and edges are removed and the resulting body is burr free.

The object is further achieved by an inductive conductivity sensor, which is produced according to one of the above described methods.

Preferably, the housing and the sleeve comprise a partially crystalline thermoplastic, especially a polyether ketone, especially polyetheretherketone (PEEK).

Alternatively, the housing and the sleeve comprise an amorphous thermoplastic, especially a polysulfone, especially polyphenylene sulfone (PPSU).

In an advantageous further development, the first end section includes at least a first weld seam, and the second end section at least two welded seams, thus a second weld seam and a third weld seam.

There are different options for ending the welding process, for instance, after expiration of a constant time, after travel of a constant path, after reaching a determined point, after consumption of a predetermined amount of energy, after a predetermined power or a combination of all of these. Preferably, welding is according to a constant path, i.e. the two components melt, for instance, always equally far into one another.

BRIEF DESCRIPTION OF THE DRAWINGS

The invention will now be explained in greater detail based on the appended drawing, the figures of which show as follows.

In the figures, equal features are provided with equal reference characters.

DETAILED DESCRIPTION IN CONJUNCTION WITH THE DRAWINGS

Shown in FIG. 1 in the form of FIGS. 1a to 1d are method steps for manufacturing a conductivity sensor. FIG. 1e shows a detail view of FIG. 1b.

FIG. 1 shows a sensor module 1 of an inductive conductivity sensor 30 with a transmitting coil 4 and a receiving coil 5, which are accommodated in a housing 2. The transmitting coil 4 and the receiving coil 5 are arranged lying opposite one another on mutually facing away sides of a circuit card 3. The transmitting- and receiving coil 4, 5 embodied as rotationally symmetric, toroidal coils are, in this way, arranged coaxially lying behind one another. The circuit card 3 includes coil contacting, conductive traces (not shown), which connect the transmitting coil 4 with a driver circuit and the receiving coil 5 with a receiving circuit. The driver circuit and the receiving circuit can be components of a sensor circuit arranged on the circuit card 3.

Housing 2 has a duct 9 passing through the transmitting coil 4 and the receiving coil 5 along their coincident axes of rotation. If the housing 2 is immersed in an electrically conductive medium 31, such surrounds the housing 2 and penetrates into the duct 9, so that a closed electrical current path passing through the two coils 4, 5 can form in the medium 9, when the transmitting coil 4 is excited with an alternating voltage, as explained above.

Figure 1A:
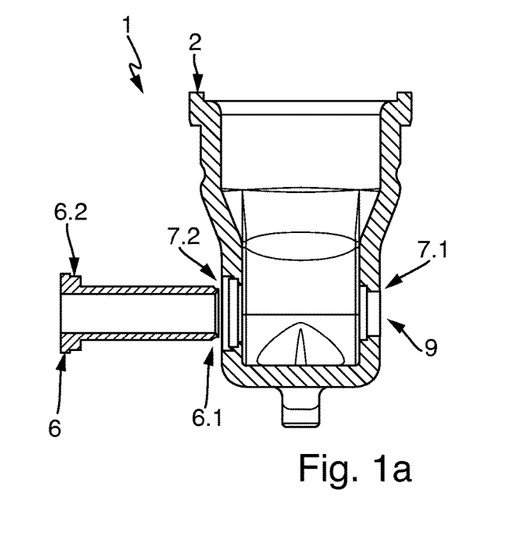
FIGS. 1a, 1b, 1c, 1d and 1e show the various stages in the manufacture of the conductivity sensor of the invention.
Figure 1B:
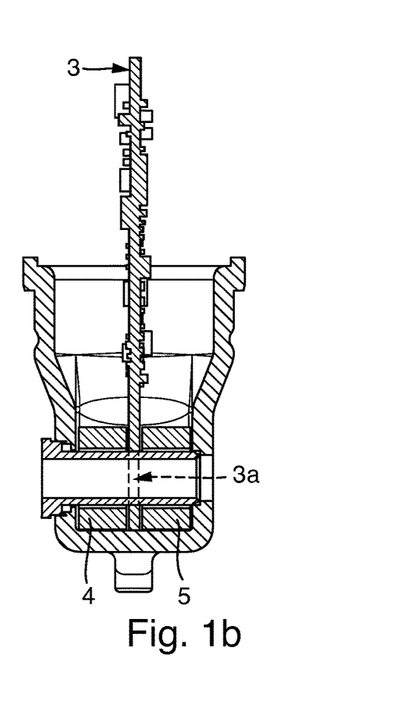
Figure 1C:
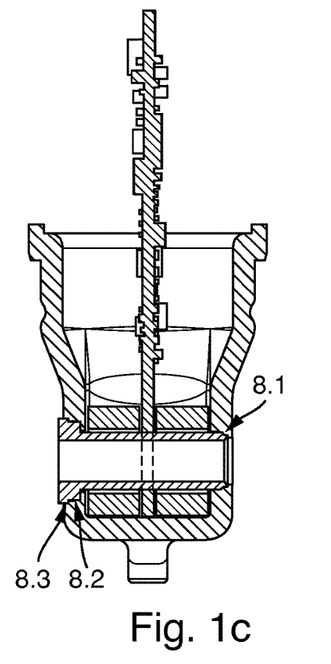

The sensor module 1 can be produced in the following manner: The circuit card 3 populated with the transmitting coil 4, the receiving coil 5 and, in given cases, additional circuit parts is placed in the housing 2 in a first step (FIG. 1b). The transmitting coil 4 and the receiving coil 5 are so arranged on the circuit card 3 that they surround an opening 3a (drawn dashed) in the circuit card 3. Housing 2 can be manufactured, for example, by means of an injection molding method. Housing 2 includes two mutually opposing openings 7.1, 7.2, which align with the opening 3a in the circuit card 3 surrounded by the toroidal coils 4, 5. A sleeve 6 is inserted through the opening 7.2 of the housing 2 and through the therewith aligned opening 3a in the circuit card 3 and out to the additional opening 7.1. Sleeve 6 includes a first end section 6.1 and a second end section 6.2, wherein the first end section 6.1 is inserted first into the housing 2. The first end section 6.1, thus, comes to rest in the first opening 7.1 and the second end section 6.2 comes to rest in the second opening 7.2. FIG. 1c shows the welded state of the first end section 6.1 with the first opening 7.1 (weld seam 8.1) and the welded state of the second end section 6.2 with the second opening 7.2 (weld seams 8.2 and 8.3). In this way, the duct 9 extending axially relative to the shared rotational axis of the transmitting and receiving coils 4, 5 is completed. In measurement operation, medium 31 flows through duct 9.

Figure 1D:
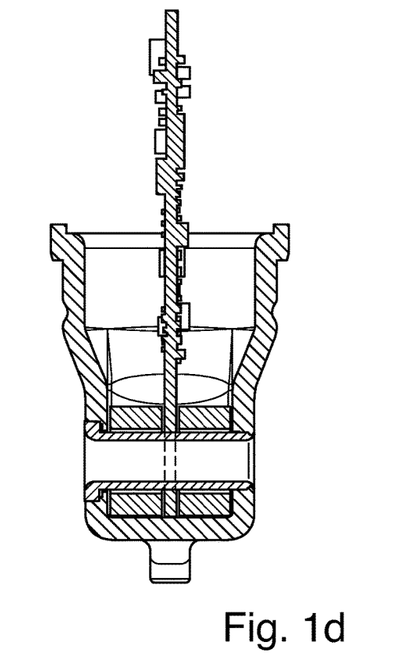

In FIG. 1d, the weld seams 8.1, 8.2, 8.3 are reworked, wherein possibly elevated particles are removed by machining. Since sleeve 6 serves in the case of an inductive conductivity sensor 1 for guiding a liquid medium through the duct 9, the radii of the sleeve 6 in the end regions 6.1, 6.2 are rounded toward the duct 9. These roundings extend, in such case, externally inwardly toward the duct 9 and improve the flow of the medium 31 flowing through the duct 9.

Both housing 2 as well as also sleeve 6 comprise a partially crystalline thermoplastic material, especially a polyether ketone, especially polyetheretherketone (PEEK) or glass fiber reinforced polyetheretherketone. Alternatively, housing 2 and sleeve 6 comprise an amorphous thermoplastic, especially a polysulfone, especially polyphenylene sulfone (PPSU).

Figure 1E:
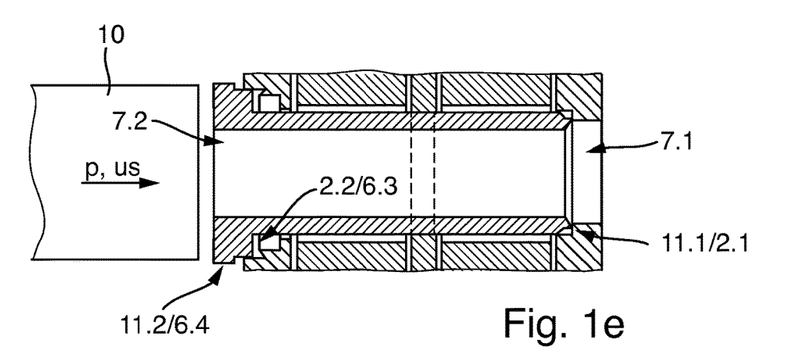
Figure 2A:
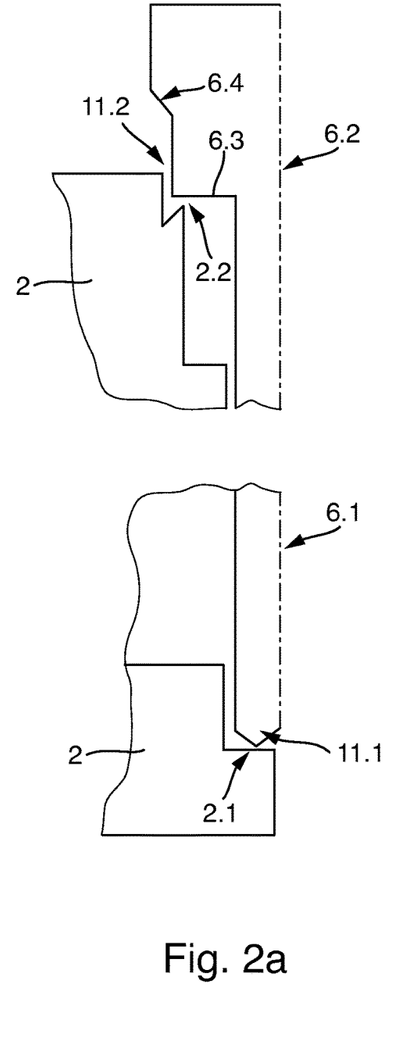
FIG. 2a shows the weld seam before welding.
Figure 2B:
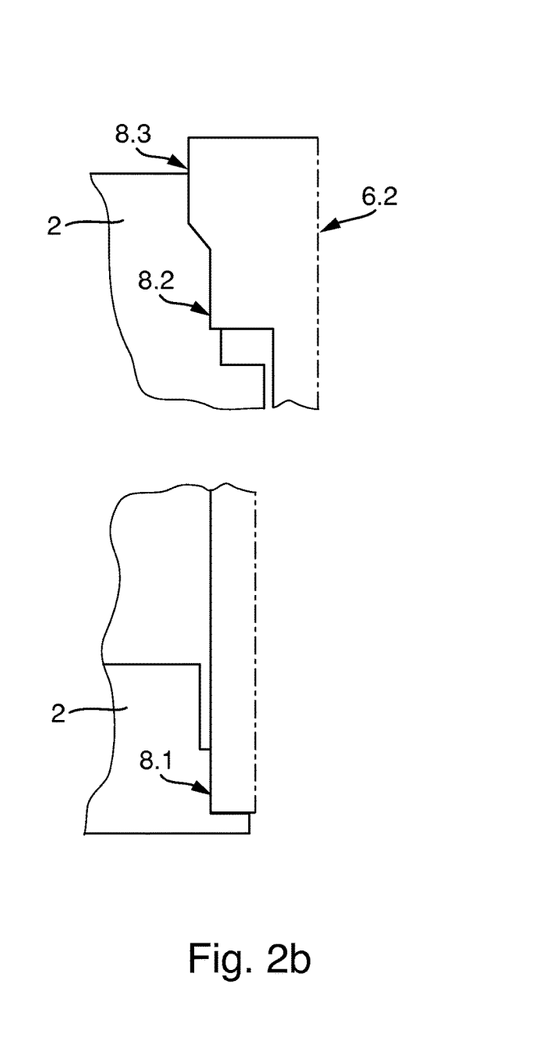
FIG. 2b shows the weld seam after welding.

Sleeve 6 is welded with the housing 2 by means of ultrasonic welding. In this regard, a sonotrode 10 is applied exclusively on the side of the second end section 7.2. Compare FIG. 1e. FIGS. 2a and 2b are detailed views respectively before and after the welding.

The first end section 6.1 of the sleeve 6 is welded with the housing 2 by means of far field welding and the second end section 6.2 of the sleeve is welded with the housing 2 by means of near field welding. The two welds occur simultaneously, i.e. the near field- and far field welding take place (virtually) simultaneously without having to turn the workpiece (thus the sleeve 6 or the housing 2) or to use additional parts or caps. In any case, the near field welding occurs during the far field welding on the same workpiece without having to change anything. Welding occurs in the time sequence, first weld seam 8.1 (far field), second weld seam 8.2 (near field) and third weld seam 8.3 (near field), wherein the first weld seam 8.1, second weld seam 8.2 and third weld seam 8.3 are for a certain time simultaneously molten.

FIG. 2 shows the respective geometries for the occurring weld seams 8.1, 8.2 and 8.3, respectively the respective concentrators 11.1 and 11.2.

FIG. 2a shows the sleeve 6 before the welding process and FIG. 2b shows the sleeve 6 after the welding process. The upper parts of the figures show the second end region 6.2, while the lower parts of the figures show the first end region 6.1 of the sleeve 6, in each case with the respective sections of the housing 2.

Shear joints are used for forming the seam geometry. The shear joint provides a sealed weld and is embodied as a step with very little contact area. This small area and the resulting high energy flow bring about a rapid melting. The sliding of the two melt surfaces relative to one another prevents hollow locations and air contact. In general, a homogeneous, tightly sealed connection is obtained.

As already mentioned the welding comprises, as a whole, three welds 8.1, 8.2 and 8.3.

The first end section 6.1 of the sleeve includes a first concentrator 11.1, and the first concentrator 11.1 serves for forming the first weld seam 8.1 with a planar area 2.1 of the housing 2.

The first concentrator 11.1 as well as, in given cases, the second concentrator 11.2 (see below) comprise a V-shaped profile having an acute angle between 90° and 60°, a triangular profile, a rectangular profile or a half round profile. Because of this profile, the concentrator can function also as an energy director. This geometry effects an initial, line shaped contact. The result is a very concentrated introduction of the ultrasonic energy and therewith a rapid heating and melting of the material.

The weld seam is nevertheless embodied as a shear joint, since the two portions to be welded slide into one another and form a medium excluding connection. There are different options for terminating the welding process, for instance, after expiration of a constant time, after travel of a constant path, after reaching of a determined point, after consumption of a predetermined amount of energy, after a predetermined power or a combination of all of these. Preferably, a constant path welding is used, i.e. the two components always melt equally far into one another. During welding, the sonotrode 10 exerts a defined pressure p with a certain ultrasonic energy US on the sleeve 6, especially on the second end section 6.2. Welding is at room temperature.

A shear joint is likewise used for the second weld seam 8.2. For forming the shear joint, the housing 2 includes a wedge shaped profile 2.2, and the sleeve 6 a second planar area 6.3 corresponding to the wedge shaped profile 2.2, wherein the resulting shear joint forms the second weld seam 8.2.

A shear joint is likewise used for the third weld seam 8.3. For forming the shear joint, the housing 2 includes a second concentrator 11.2, and the second concentrator 11.2 serves for forming the third weld seam 8.3 with an inclined area 6.4 of the sleeve 6 in the region of the second end section 6.2. "Inclined" in this connection means inclined in the cross section relative to the direction of introduction.

Figure 3:
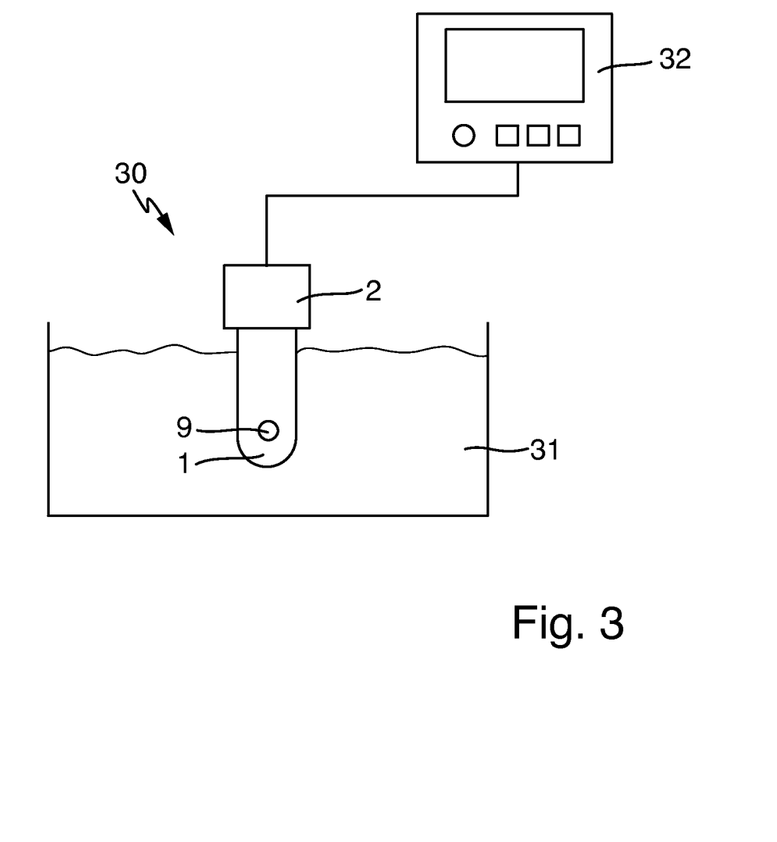
FIG. 3 shows the conductivity sensor in measurement operation.

FIG. 3 shows schematically a conductivity sensor 30 with a housing module 1 for immersion in a medium 31. Accommodated in the housing module 1 are the transmitting and receiving coils, as well as, in given cases, at least parts of the driver circuit exciting the transmitting coil with an alternating voltage and at least parts of the receiving circuit connected with the receiving coil and serving for registering and conditioning a signal induced in the receiving coil and dependent on the conductivity of the medium 31. The housing module 1 forms a duct 9 passing through the coils contained in the housing module 1. Medium 31 flows through duct 9, when the housing module 1 is immersed in the medium 31, such as shown in FIG. 3. Medium 31 can be located in a container, especially in a pipe or a reaction container, in a production plant. The conductivity sensor 30 is then held in a retractable assembly integrated in the pipe, respectively container, wall and inserted into the medium 31 contained in the pipe or container.

The sensor circuit contained in the housing module 1 is connected via a cable connection with a superordinated unit, in the present example with a measurement transmitter 32. The superordinated unit can also be a computer or a programmable logic controller. The connection between the conductivity sensor 30 and the superordinated unit can also be a wireless connection. In this case, the superordinated unit can also be a portable device, especially also an Internet- or radio capable telephone, such as e.g. a smart phone. The superordinated unit serves for supplying the sensor- and the driver circuit with energy, as well as for registering and additional processing, especially also for display, of measured values registered by the conductivity sensor 30.

The conductivity sensor 30 is connected, for instance, via a cable, for instance, via a galvanically isolated interface, especially an inductive interface, with a measurement transmitter 32. The measurement transmitter is, in turn, connected via a bus connection, such as Fieldbus Foundation, ModBus, HART or like bus connection, to a control system. Alternatively, the conductivity sensor can also be directly connected via a bus connection to a control system.

The invention claimed is:

1. A method for manufacturing an inductive conductivity sensor, the sensor including a circuit board, wherein on both sides of the circuit board coils are placed surrounding an opening of the circuit board, the circuit board with the coils disposed in a housing having an opening, the method comprising:
   inserting a sleeve through the opening of the housing and through the opening of the circuit board into the housing, the sleeve having a first end section and a second end section, wherein the sleeve is inserted with the first end section first into the housing;
   welding the sleeve to the housing using a sonotrode by ultrasonic welding; and
   simultaneously welding the first end section to the housing by far field welding and the second end section to the housing by near field welding, wherein:
      the sonotrode is applied exclusively on the sleeve on a side of the second end section;
      the first end section of the sleeve includes a first concentrator adapted to enable forming a first shear joint with a first planar area of the housing at or near the first end section, the first shear joint defining a first weld seam; and
      the housing includes a wedge-shaped profile in an area contacted by the second end section of the sleeve, the wedge-shaped profile adapted to enable forming a second shear joint with a second planar area of the second end section, the second shear joint defining a second weld seam.

2. The method as claimed in claim 1, wherein:
   a third shear joint is used for forming a seam geometry of a third weld seam; and
   the housing includes a second concentrator, and the second concentrator enables forming the third weld seam with an inclined area of the sleeve at or near the second end section.

3. The method as claimed in claim 1, wherein:
   at least one of the concentrators has one of:
   a V-shaped profile with an acute angle between 90° and 60°, a triangular profile, a rectangular profile and a half round profile.

4. The method as claimed in claim 1, wherein:
   the welding proceeds in a time sequence of first weld seam, second weld seam, and third weld seam; and
   the first weld seam, second weld seam and third weld seam are for a certain time simultaneously molten.

5. The method as claimed in claim 1, wherein:
   welding occurs at room temperature.

6. The method as claimed in claim 1, wherein:
the sleeve welded with the housing is further worked, especially rounded, in the first end region and/or in the second end region.

7. The method as claimed in claim 1, wherein the housing and the sleeve are of a partially crystalline thermoplastic.

8. The method as claimed in claim 7, wherein the partially crystalline thermoplastic is polyetheretherketone (PEEK).

9. The method as claimed in claim 1, wherein the first concentrator and the wedge-shaped profile are adapted to provide substantially equal energy from the sonotrode to the first end section and the second end section in forming the first weld seam and the second weld seam, respectively.

* * * * *